(12) United States Patent
Popovic et al.

(10) Patent No.: US 10,888,307 B2
(45) Date of Patent: Jan. 12, 2021

(54) SYSTEM FOR PERFORMING INTRALUMINAL CORONARY AND METHOD OF OPERATION THEREOF

(71) Applicant: KONINKLIJKE PHILIPS N.V., Eindhoven (NL)

(72) Inventors: Aleksandra Popovic, Boston, MA (US); Ralf Seip, Carmel, NY (US); David Paul Noonan, New York, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1128 days.

(21) Appl. No.: 15/119,077

(22) PCT Filed: Feb. 26, 2015

(86) PCT No.: PCT/IB2015/051413
§ 371 (c)(1),
(2) Date: Aug. 15, 2016

(87) PCT Pub. No.: WO2015/128817
PCT Pub. Date: Sep. 3, 2015

(65) Prior Publication Data
US 2017/0042521 A1 Feb. 16, 2017

Related U.S. Application Data

(60) Provisional application No. 61/944,774, filed on Feb. 26, 2014.

(51) Int. Cl.
*A61B 17/00* (2006.01)
*A61B 17/11* (2006.01)
(Continued)

(52) U.S. Cl.
CPC ........ *A61B 17/00234* (2013.01); *A61B 17/11* (2013.01); *A61B 17/1204* (2013.01);
(Continued)

(58) Field of Classification Search
CPC .............. A61B 17/00234; A61B 17/11; A61B 17/1204; A61B 17/12109;
(Continued)

(56) References Cited

U.S. PATENT DOCUMENTS 5,964,750 A * 10/1999 Tulleken ................. A61B 18/24
606/15
2008/0195230 A1 * 8/2008 Quijano ............. A61B 17/3203
623/23.72

(Continued)

FOREIGN PATENT DOCUMENTS

EP 1591069 A1 11/2005
WO 2012088501 A2 6/2012
(Continued)

*Primary Examiner* — Linda C Dvorak
*Assistant Examiner* — Bradford C. Blaise

(57) ABSTRACT

A method of performing a coronary bypass procedure is performed by a flexible apparatus controlled by at least one controller, the method may include acts of: percutaneously situating the flexible apparatus into a first artery coupled to connective tissue of a chest wall; transluminally detaching at least a portion of the first artery from the connective tissue by applying ultrasound signals of a first type emitted by at least one transducer of the flexible apparatus; steering at least a portion of the detached portion first artery from a current location to a bypass location at a target artery by applying a force transmitted through the flexible apparatus situated within the first artery; and coupling, by the flexible apparatus situated within the first artery, the first artery to the target artery at the bypass location to establish flow communication between the first artery and the target artery.

16 Claims, 10 Drawing Sheets

(51) Int. Cl.
*A61B 17/12* (2006.01)
*A61B 18/24* (2006.01)
*A61N 7/02* (2006.01)
*A61B 17/22* (2006.01)
*A61B 34/20* (2016.01)
*A61B 17/32* (2006.01)
*A61B 17/30* (2006.01)

(52) U.S. Cl.
CPC .. *A61B 17/12109* (2013.01); *A61B 17/12136* (2013.01); *A61B 17/22012* (2013.01); *A61B 18/24* (2013.01); *A61B 34/20* (2016.02); *A61N 7/022* (2013.01); *A61B 2017/00252* (2013.01); *A61B 2017/1107* (2013.01); *A61B 2017/22014* (2013.01); *A61B 2017/306* (2013.01); *A61B 2017/32007* (2017.08); *A61B 2017/320069* (2017.08); *A61B 2017/320082* (2017.08); *A61B 2034/2051* (2016.02); *A61B 2217/005* (2013.01)

(58) Field of Classification Search
CPC ........ A61B 17/12136; A61B 17/22012; A61B 17/320068; A61B 2017/32007; A61B 2017/320082; A61B 2017/320069; A61B 2017/00252; A61B 2017/1107; A61B 2017/22014; A61B 2017/306; A61B 18/24; A61B 34/20; A61B 2034/2051; A61B 2217/005; A61N 7/022; A61N 2007/027

See application file for complete search history.

(56) References Cited

U.S. PATENT DOCUMENTS

| | | |
|---|---|---|
| 2009/0230823 A1 | 9/2009 | Kushculey |
| 2010/0069820 A1 | 3/2010 | Zotz |
| 2010/0198241 A1 | 8/2010 | Gerrah |
| 2014/0005706 A1 | 1/2014 | Gelfand |
| 2014/0058294 A1* | 2/2014 | Gross ..................... A61N 7/022 601/2 |
| 2014/0100459 A1* | 4/2014 | Xu ..................... A61B 17/2258 600/439 |
| 2015/0025518 A1 | 1/2015 | Kobayashi |

FOREIGN PATENT DOCUMENTS

| | | |
|---|---|---|
| WO | 2012120495 A2 | 9/2012 |
| WO | 2015128751 A1 | 9/2015 |
| WO | 2015128766 A1 | 9/2015 |

* cited by examiner

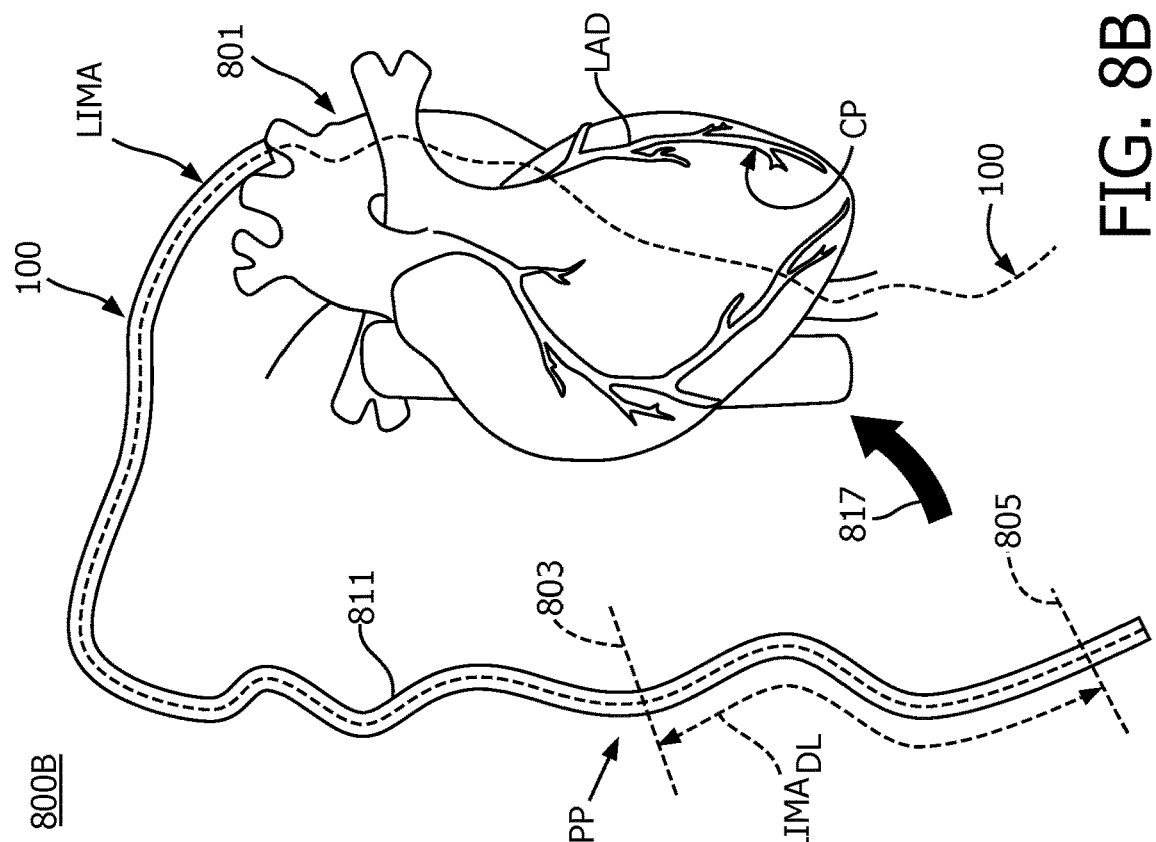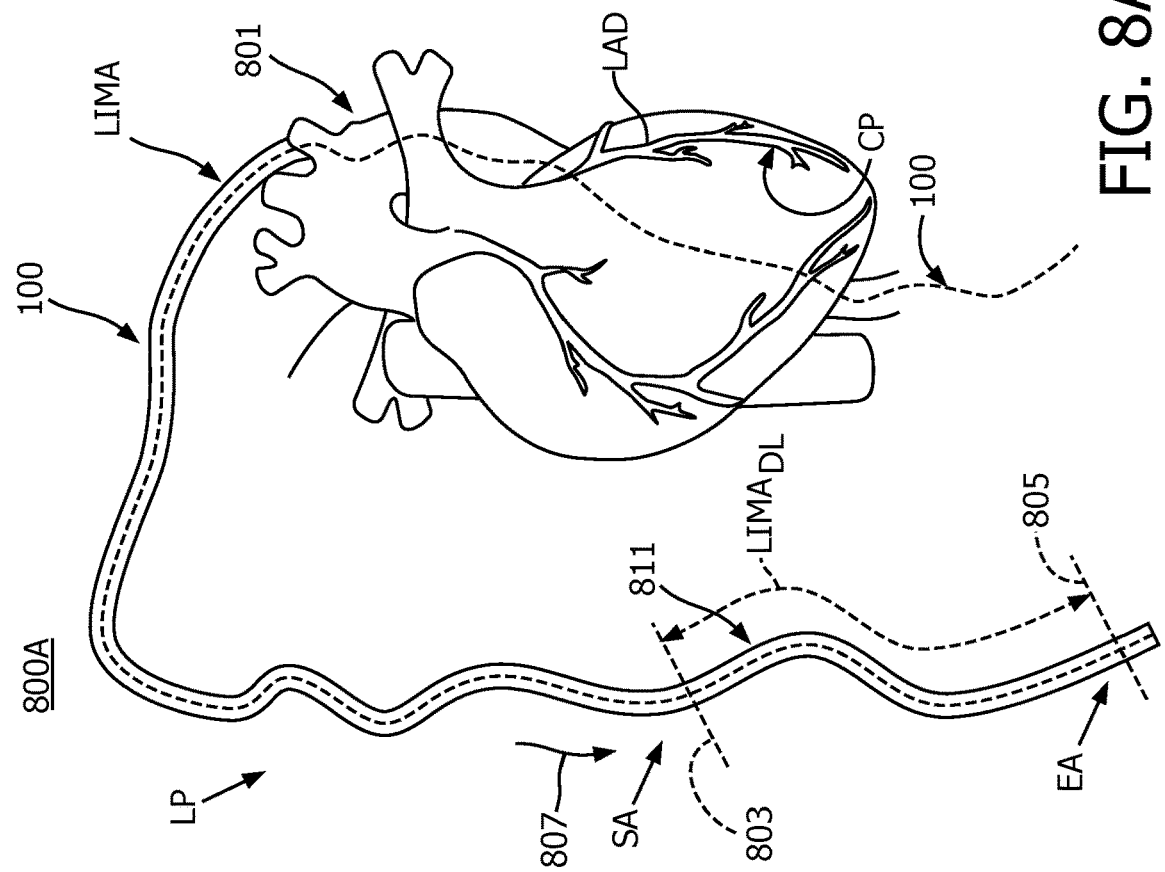

SYSTEM FOR PERFORMING INTRALUMINAL CORONARY AND METHOD OF OPERATION THEREOF

CROSS-REFERENCE TO PRIOR APPLICATIONS

This application is the U.S. National Phase application under 35 U.S.C. § 371 of International Application No. PCT/IB2015/051413, filed on Feb. 26, 2015, which claims the benefit of U.S. Provisional Patent Application No. 61/944,774, filed on Feb. 26, 2014. These applications are hereby incorporated by reference herein.

The present system relates to system for performing revascularization and, more particularly, to a system for performing myocardial revascularization using an artery such as a left internal mammary artery (LIMA) that is harvested using transluminal cauterization technique, and a method of operation thereof.

BACKGROUND

Coronary artery disease is caused by plaque build-up in the coronary arteries supplying blood to the heart muscle. As the result, oxygenation of the muscle is insufficient, resulting in chronic angina and myocardial infarction. Coronary revascularization is a procedure to re-establish the blood flow to the heart muscle. In percutaneous coronary intervention, stents are placed in the diseased areas to open up the artery. In bypass surgery, a new conduit is proximally attached to the aorta and distally to the coronary artery thus bypassing the plaque. The most patent conduit is the left internal mammary artery (LIMA). LIMA supplies blood from the aorta to the chest muscles. Due to its patency, LIMA may be used to bypass the Left Anterior Descending artery (LAD), which supplies 60% of blood to the left ventricle. Such procedures are known as LIMA-to-LAD (LIMA-LAD) bypass and have significantly better outcomes when compared to any other revascularization technique such as percutaneous in-situ coronary bypass through harvested veins.

Despite its efficacy in terms of reducing risk from major cardiovascular events, open surgery LIMA-LAD bypass is currently performed significantly less frequently then stenting due to the invasiveness of the procedure. Similarly, while minimally invasive LIMA-LAD bypass is less invasive than open surgery, it is more invasive than stenting and poses technical challenges for the surgeon.

When performing LIMA-LAD bypass using a minimally invasive surgery approach, a key challenge is how the LIMA is mechanically detached from the surrounding tissue given the limited workspace within the thoracic cavity, rigid instrumentation, limited visualization and the requirement to remove significant length of the vessel. During the removal process, these factors may lead to operator error and consequently damage of the vessel, which can limit its usefulness for grafting.

SUMMARY

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a method of performing a bypass procedure, the method may be performed by a flexible apparatus controlled by at least one controller, the method may include one or more acts of: percutaneously situating the flexible apparatus into a first artery (LIMA) which is coupled to connective tissue of a chest wall; transluminally detaching at least a portion of the first artery from the connective tissue of the chest wall by applying ultrasound signals of a first type emitted by at least one transducer of the flexible apparatus; steering at least a portion of the detached portion of the first artery from a current location to a bypass location at a target artery by applying a force transmitted through the flexible apparatus situated within the first artery; and coupling, by the flexible apparatus situated within the first artery, the first artery to the target artery (LAD) at the bypass location (CP) to establish flow communication between the first artery and the target artery.

The method may further include an act of interrupting blood flow to the first artery by inflating a balloon situated about an outer periphery of the flexible apparatus and configured to at least partially interrupt blood flow. The method may further include an act of establishing a port in the target artery at the bypass location using one of an arterial puncture device and a laser arteriectomy device located at a distal end of the flexible device and adjacent to the target artery. The method may further include an act of inserting a stent graft through a channel in the flexible apparatus and at least partially through the port in the target artery. It is further envisioned that the method may include an act of transluminally cauterizing side branches of the first artery by applying ultrasound signals of a second type emitted by the at least one transducer of the flexible apparatus. In accordance with embodiments of the present system, the ultrasound signals of the first type may include histotripsy pulses and the ultrasound signals of the second type may include high-intensity focused ultrasound (HIFU) pulses that are lower in intensity and longer in duration than the ultrasound signals of the first type. It is also envisioned that the first artery may be a left internal mammary artery (LIMA) and the target artery may be a left anterior descending artery (LAD) so as to perform a LIMA-LAD bypass.

In accordance with yet other embodiments of the present system, there is disclosed a flexible apparatus for performing a bypass procedure such as a coronary bypass procedure, the apparatus may include at least one controller which may be configured: percutaneously locate the flexible apparatus into at least one desired location of a first artery (LIMA) which is coupled to connective tissue of a chest wall; drive at least one transducer (142) to emit ultrasound signals of a first type to transluminally detach at least a portion of the first artery from the connective tissue; steer the flexible apparatus to move at least a portion of the detached portion of the first artery from a current location to a bypass location (CP) at a target artery (LAD) by applying a force to the first artery, the force include a force from at least one steering actuator controlled by the at least one controller; and couple the first artery to the target artery at the bypass location to establish flow communication between the first artery and the target artery.

It is further envisioned that the at least one controller may be further configured to interrupt blood flow to the first artery by inflating a balloon situated about an outer periphery of the flexible apparatus and configured to at least partially interrupt blood flow. In accordance with some embodiments, the at least one controller may be further configured to establish a port in the target artery at the bypass location using one of an arterial puncture device and a laser arteriectomy device. It is also envisioned that the at least one controller may be further configured to insert a stent graft through a channel in the flexible apparatus and at least partially through the port in the target artery. Moreover, it is envisioned that the at least one controller may be further configured to transluminally cauterize side branches of the first artery by applying ultrasound signals of a second type emitted by the at least one transducer. It is also envisioned that the at least one controller may be further configured to drive the at least one transducer such that the ultrasound signals of the first type include histotripsy pulses and the ultrasound signals of the second type include high-intensity focused ultrasound (HIFU) pulses that are lower in intensity and longer in duration than the ultrasound signals of the first type.

In accordance with yet further embodiments of the present system, there is provided a computer program stored on a computer readable memory medium, the computer program may be configured to control a flexible apparatus to perform a bypass procedure, the computer program may include: a program portion configured to control the flexible apparatus to: percutaneously locate the flexible apparatus into a first artery (LIMA) which is coupled to connective tissue of a chest wall; transluminally detach at least a portion of the first artery from the connective tissue of the chest wall by applying ultrasound signals of a first type emitted by at least one transducer (142) of the flexible apparatus; steer at least a portion of the detached portion first artery from a current location to a bypass location at a target artery by applying a force transmitted through the flexible apparatus situated within the first artery; and couple, by the flexible apparatus situated within the first artery, the first artery to the target artery (LAD) at the bypass location (CP) to establish flow communication between the first artery and the target artery.

In accordance with yet other embodiments, the program portion may be further configured to interrupt blood flow to the first artery by inflating a balloon situated about an outer periphery of the flexible apparatus and configured to at least partially interrupt blood flow. It is also envisioned that the program portion may be further configured to establish a port in the target artery at the bypass location using one of an arterial puncture device and a laser arteriectomy device. In some embodiments, the program portion may be further configured to insert a stent graft through a channel in the flexible apparatus and at least partially through the port in the target artery. In yet other embodiments, the program portion may be further configured to transluminally cauterize side branches of the first artery by applying ultrasound signals of a second type emitted by the at least one transducer of the flexible apparatus. In accordance with some embodiments the ultrasound signals of the first type may include histotripsy pulses and the ultrasound signals of the second type may include high-intensity focused ultrasound (HIFU) pulses that are lower in intensity and longer in duration than the ultrasound signals of the first type.

BRIEF DESCRIPTION OF THE DRAWINGS

The present invention is explained in further detail in the following exemplary embodiments and with reference to the FIGS., where identical or similar elements are partly indicated by the same reference numerals, and the features of various exemplary embodiments being combinable. In the drawings:

FIG. 8A shows the catheter during use performing acts of process 700 in accordance with embodiments of the present system;

FIG. 8B shows the catheter during use performing acts of process 700 in accordance with embodiments of the present system;

DETAILED DESCRIPTION

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. Further, in some figures, crosshatching may be omitted for the sake of clarity. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1:
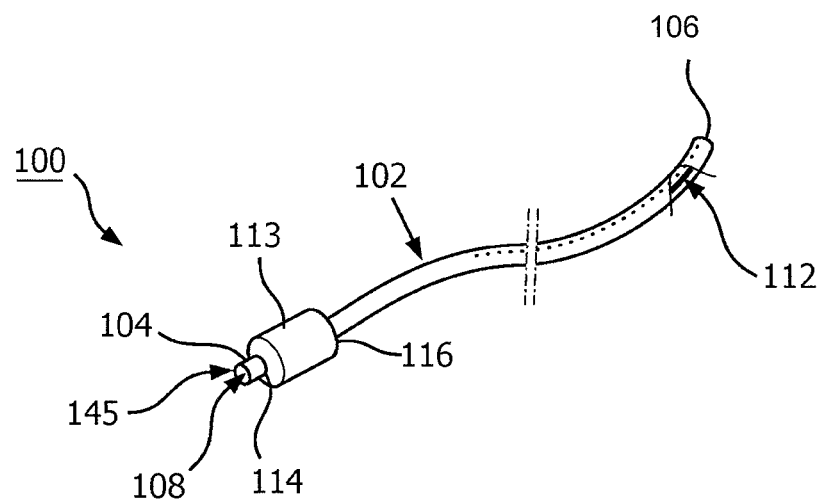
FIG. 1 shows a partially cutaway perspective view of a portion of a catheter in accordance with embodiments of the present system.

FIG. 1 shows a partially cutaway perspective view of a portion of a catheter 100 in accordance with embodiments of the present system. The catheter 100 may include one or more of a body 102, a balloon 113, an optional base, a controller, and an optional at least one instrument such as an ultrasound transducer array (UTA), etc. The body 102 may be a flexible, steerable catheter and/or a pre-shaped catheter or snake-like robot and may be steered using active and/or passive methods. For example, in some embodiments the controller may be configured to steer one or more portions of the body 102. In some embodiments, it is envisioned that the body 102 may include steering actuation portions (e.g., electro-active polymers (EAPs), guide cables, etc.) to exert a force upon portions of the body 102 to steer corresponding portions of the body 102 in a desired direction under the control of the controller. The body 102 may include at least one channel 112 located between proximal and distal ends 106 and 104, respectively. At least one distal opening 108 may be located at the distal end 104 of the body 102 and at least one proximal opening may be located at the proximal end 106.

The UTA may be configured to enable LIMA takedown as described in copending U.S. application Ser. No. 15/119,039, entitled "SYSTEM FOR PERFORMING INTRALUMINAL HISTOTRIPSY AND METHOD OF OPERATION THEREOF" the contents of which are incorporated herein by reference.

The at least one channel 112 may include a hollow channel which may be configured to provide for at least one instrument to pass through it such as the UTA. For example, in accordance with embodiments of the present system the at least one instrument may be inserted and removed from the at least one channel 112.

In accordance with embodiments of the present system, the at least one instrument may include instruments such as one or more of a puncture device configured to form a distal end opening in the LIMA and a port to target an artery such as the LAD, a trans-catheter cauterizer to cauterize desired tissue, the UTA, an optional camera such as a two- or three-dimensional (2D or 3D) camera. The camera may be utilized to obtain still and/or video images which may be displayed on a rendering device such as a display, and other instruments as may be desired by a user such as a stent applicator configured to apply a stent to a desired location. The camera may communicate with the controller using wired and/or wireless communication methods to transmit image information to the controller for further processing. In some embodiments, one or more functionalities of the catheter 100 may be integrated in a single device configured to perform the one or more functionalities without requiring the removal and/or insertion of certain components such as the at least one instrument during use (e.g., during surgery as opposed to setup). With regard to the functionalities, the functionalities may include stopping (or substantially stopping) blood-flow, steering, puncturing and/or porting arteries, cauterizing, LIMA takedown, LIMA steering, arterial coupling, stenting (e.g., inserting one or more stents), fenstrating, imaging, etc. The at least one channel 112 may be further configured to receive a stent such as an endoluminal stent graft as is described herein. In some embodiments, it is envisioned that a plurality of instruments may be situated within individual corresponding channels, a single channel of the at least one channel 112 may be shared by two or more instruments or any combination of shared and corresponding channels for instruments may be utilized.

However, in yet other embodiments the catheter 100 may include a guidewire that is configured to provide a guide path for devices such as a trans-catheter cauterizer, at least one ultrasound transducer, and flexible steering device may be provided. For example, the guidewire may be positioned leading to a location and the catheter 100 may be fed along the guidewire to arrive at the location as is readily appreciated.

The balloon 113 may be configured to expand (e.g., from a contracted position) to block blood flow in an artery such as the LIMA, when desired. The balloon 113 is shown expanded for the sake of clarity, and, in use, the balloon 113 may fit substantially flush with an outside peripheral wall of the body 102 when not expanded. The balloon 113 may be situated at a desired location relative to the body 102 such as close to the distal end 104 of the body 102.

Figure 2:
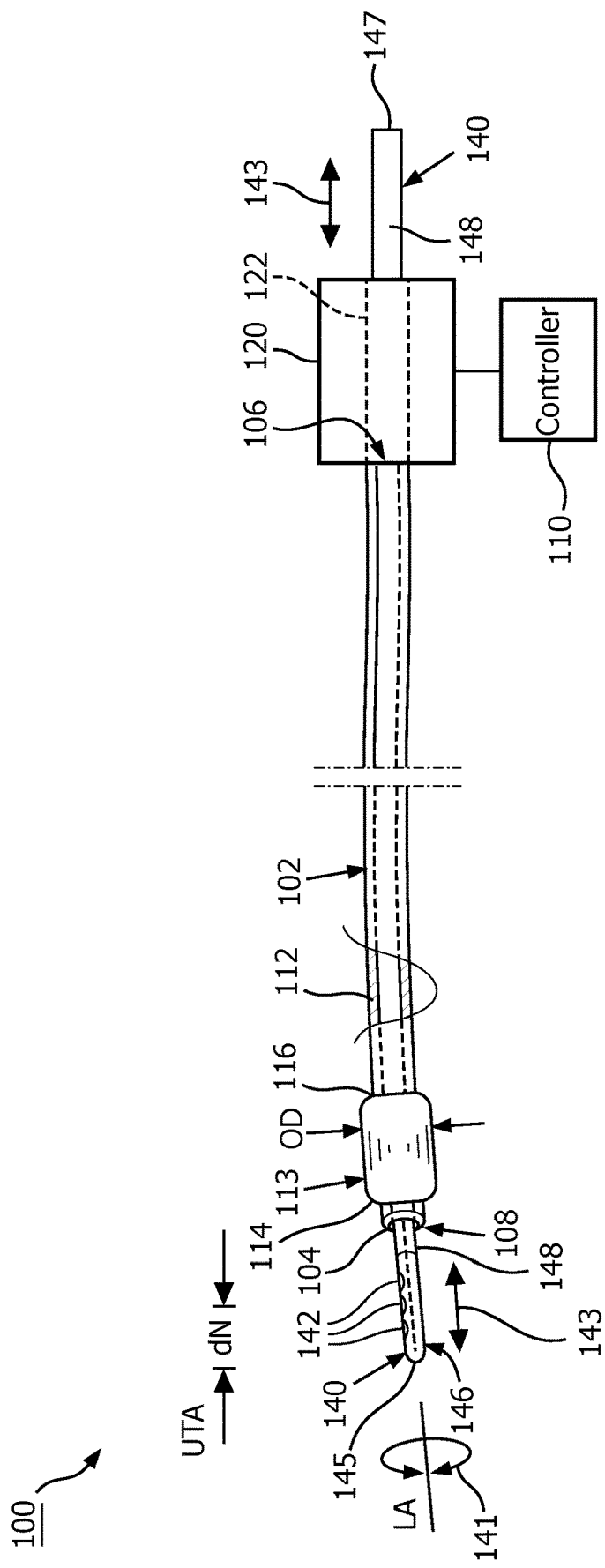
FIG. 2 is a partially cutaway side view of a portion of the catheter in accordance with embodiments of the present system.

FIG. 2 is a partially cutaway side view of a portion of the catheter 100 in accordance with embodiments of the present system. The body 102 may be coupled to the base 120 at a proximal end 106 of the body 102. The base 120 may include at least one opening through which the at least one opening 112 may be accessed. Accordingly, an optional instrument such as a UTA 140 may pass through the at least one opening 112.

A controller 110 may include one or more processors which may be local and/or distributed and may be configured to control operation of the catheter 100 and/or the at least one instrument. For example, in some embodiments, the controller 110 may control actuators to actively steer the body 102 of the catheter to a desired location and/or orientation in accordance with instructions which may be stored in a memory of the system. A real-time guidance system (e.g., a real-time guided imaging system such as an ultrasound, computed tomography (CT), and/or magnetic resonance imaging (MRI) real-time guided imaging systems) may provide information related to a location and/or orientation of the catheter 100 relative to a body in which it is located in real time and form corresponding location information for the convenience of a user and/or for further processing by the system.

In further embodiments, it is envisioned that the controller 110 may control at least one of the instruments such as a UTA 140. The UTA 140 which may have proximal and distal ends 147 and 145, respectively, a body 148, and a transducer array (TA) 146. The transducer array 146 may be coupled to the body 148 of the UTA 140 such that the transducer array 146 may be situated at the distal end 145 of the UTA 140. The transducer array 146 may include at least one transducer 142 which may be driven by the controller 110 to output focused ultrasound signals in a desired location (e.g., a focal zone) such as a location that is located beyond (e.g., outside of) a vessel wall of the ITA. The ultrasound signals may include a series of ultrasound pulses.

Further, the UTA 140 may be configured such that at least the transducer array 146 may be rotated about a longitudinal axis (La) 141 of the transducer array 146 (e.g., a full 360 degrees). Accordingly, in some embodiments, the body transducer array 146 and the body 148 coupled thereto may be rotationally coupled to the body 102 so that the transducer array 146 and the body 148 of the UTA 140 may rotate relative to the body 102 (e.g., under the control of the controller 110 and/or a user). However, in yet other embodiments, it is envisioned that the transducer array 146 may be rotationally coupled to the body 148 of the UTA 140 so that the transducer array 146 may rotate relative to the body 148 of the UTA 140. Accordingly, the transducer array 146 may be coupled to the body 148 of the UTA 140 using a rotational coupler. Further, a motor may be provided to apply a force to rotate at least the transducer array 146 relative to the body 148 of the UTA 140 and/or body 102 and may be controlled by the controller 110. In yet other embodiments, it is envisioned that a control cable may be used to transfer a force from a handle (e.g., which may be grasped by the user) to a transducer array 146 to cause the transducer array 146 to rotate about its longitudinal axis La 141.

The catheter 100 may be further configured such that the UTA 140 or portions thereof such as the transducer array 146 and/or the body 148 of the UTA 140 coupled thereto may be slideably coupled to the body 102 so that the transducer array 146 and/or the body 148 coupled thereto may telescope or otherwise slide in one or more directions relative to the body 102 as illustrated by arrow 143. In some embodiments, movement of the telescopic array 146 (rotational and/or transverse) may be monitored by sensors which may provide corresponding information to the controller 110 for further processing. Thus, for example, the controller 110 may determine a position (e.g., transverse and/or rotational) relative to, for example, the bodies of the UTA and/or catheter 148 and 102, respectively. This information may be used to determine movement of the transducer array 146 during use. For example, after the transducer array 146 is determined to rotate a full 360 degrees (or other amount e.g., 720, etc.) while transducers 142 are driven to output a desired signal to fractionate at least one cylindrical region of connective tissue, the process may withdraw the transducer array 146 by a withdrawal distance (e.g., which may be limited to an inter transducer distance such as $D_w$) so that another cylindrical (e.g., an adjacent) region of connective tissue may be similarly fractionated. In yet other embodiments, as the transducers 142 of the transducer array 140 are driven and/or rotated about the longitudinal axis La, a back-and-forth motion as illustrated by the arrow 143 may be established by the controller 110 and/or manually by the user. Thus, for example, in some embodiments, the movement of the transducer array 146 may be controlled by the controller 110 based upon sensory information and/or operating instructions derived by a process of the catheter 100. However, in yet other embodiments, the movement of the transducer array 146 may be controlled by the user directly or via the controller 110 for example using fly-by-wire controls.

The catheter 100 may further include one or more sensors for providing corresponding sensor information to the controller 110. The sensors may sense position (e.g., linear, rotational, etc.) of one or more portions of the catheter 100. Further, the sensors may sense operating parameters of the catheter 100. The catheter 100 may further include a user interface (UI) with which a user may interact with the catheter 100 to, for example, control position of the body 102 (or portions thereof) and/or position/control of one or more of the instruments, such as the UTA 140, or portions thereof, etc. The user interface may include a fly-by-wire type user interface and/or a mechanical-type user interface. Additionally, the controller may form a graphical user interface (GUI) with which a user may interact to change, for example, operating parameters of the catheter 100 in real-time.

In some embodiments, the body 102 may be configured such that its outside diameter (OD) may be slightly smaller than an inside diameter of the LIMA so that a snug fit may be established. For example, in some embodiments the OD may be about 3 mm. However, other diameters are also envisioned.

Figure 3:
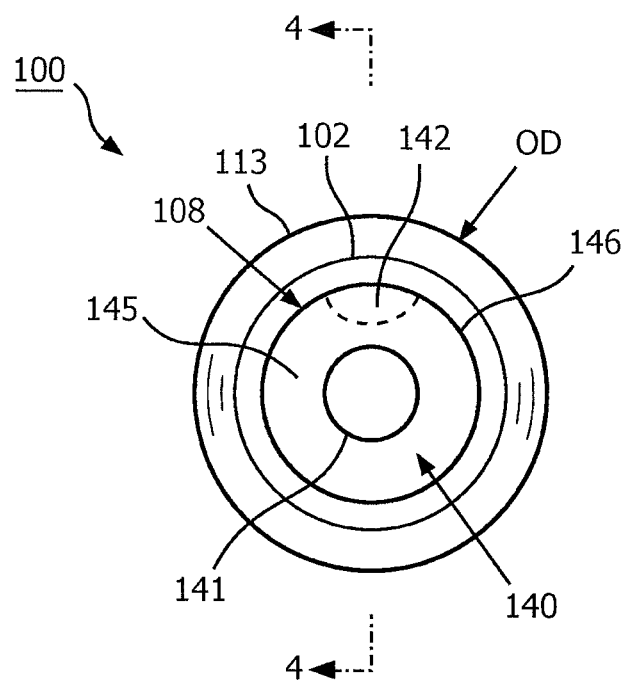
FIG. 3 is an end view of a portion of the catheter shown in FIG. 2 in accordance with embodiments of the present system.

FIG. 3 is an end view of a portion of the catheter 100 shown in FIG. 2 in accordance with embodiments of the present system. The body 102 of the catheter 100 may have any suitable cross-sectional shape such as a round or substantially round cross-sectional shape. In some embodiments, the distal opening 108 may include a single opening. However, in yet other embodiments, the distal opening 108 may include a plurality of openings. In some embodiments, instruments may be inserted and/or removed from the same distal opening. However, in yet other embodiments, one or more openings may be provided to receive corresponding instruments. Accordingly, a first instrument may be extended and/or retracted from a first distal opening and an other instrument may be extended and/or retracted from an other distal opening.

Figure 4:
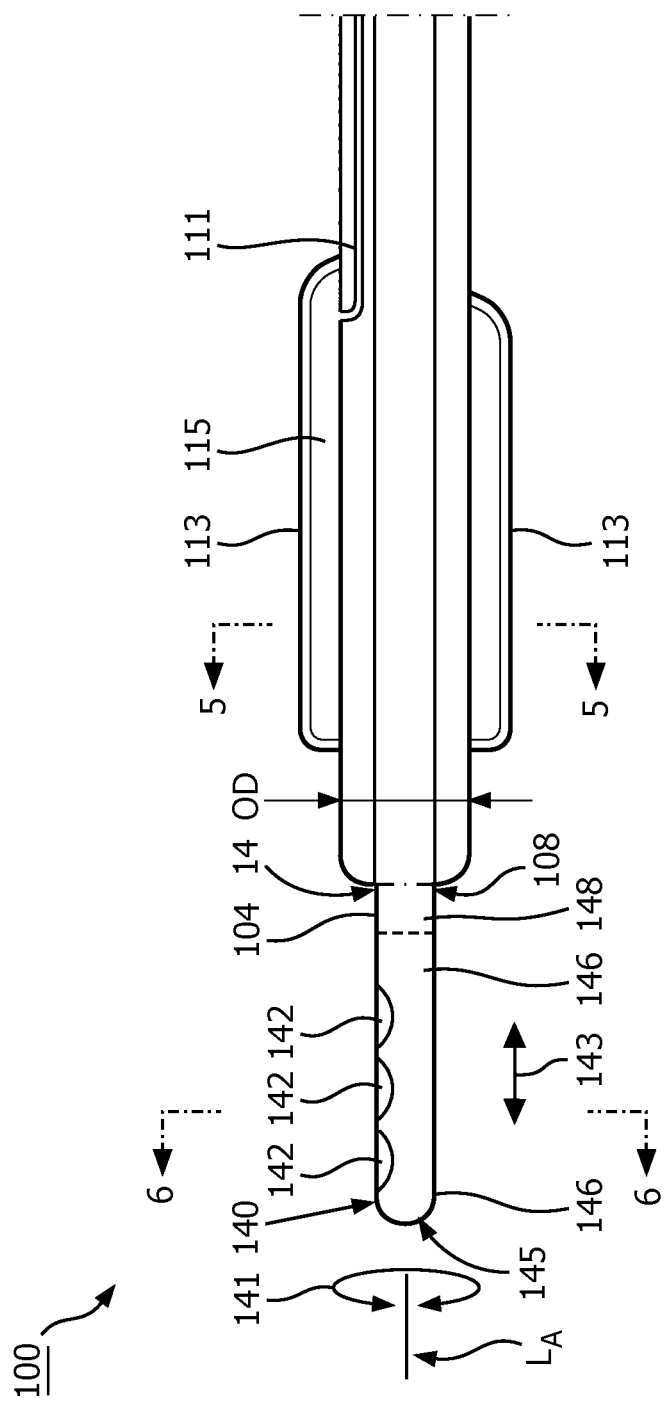
FIG. 4 is a cutaway side view of a portion of the catheter taken along lines 4-4 of FIG. 3 in accordance with embodiments of the present system.

FIG. 4 is a cutaway side view of a portion of the catheter 100 taken along lines 4-4 of FIG. 3 in accordance with embodiments of the present system. The balloon 113 may include a cavity 115 which may be flow coupled to a balloon actuator via a channel 111 through which a fluid and/or gas may pass as provided by the balloon actuator such as a pump to inflate and/or deflate the balloon 113. The balloon actuator may be controlled by the controller 110, may be controlled manually by a user, or the balloon actuator may be controlled by a combination of the controller 110 and the user.

Figure 5:
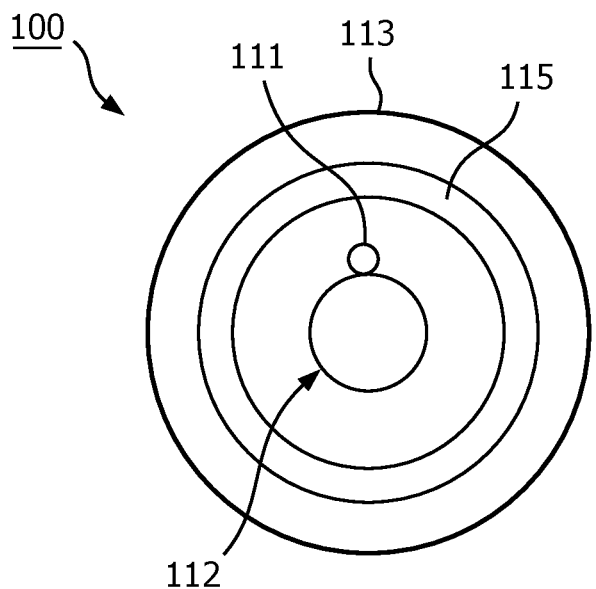
FIG. 5 is a cutaway side view of a portion of the catheter taken along lines 5-5 of FIG. 4 in accordance with embodiments of the present system.

FIG. 5 is a cutaway side view of a portion of the catheter 100 taken along lines 5-5 of FIG. 4 in accordance with embodiments of the present system. The channel 111 may be located in any suitable location and/or may have any desired cross-section such as a round cross-section. The UTA 140 is not shown for the sake of clarity.

Figure 6:
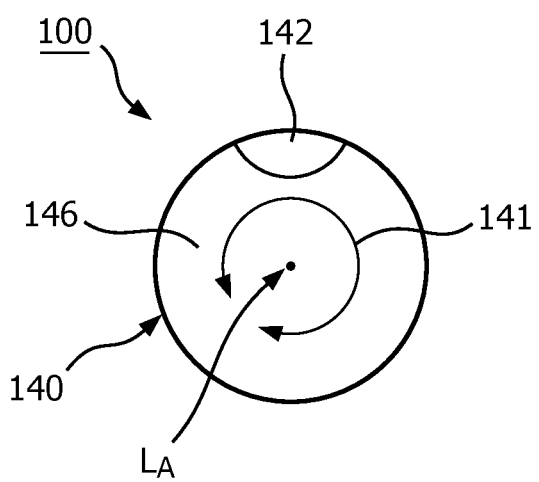
FIG. 6 is a cutaway side view of a portion of the transducer array of an ultrasound transducer array (UTA) taken along lines 6-6 of FIG. 4 in accordance with embodiments of the present system.

FIG. 6 is a cutaway side view of a portion of the transducer array 146 of the UTA 140 taken along lines 6-6 of FIG. 4 in accordance with embodiments of the present system. The transducers 142 may be aligned in a row and may include a series of spherical and/or truncated spherical section ultrasound transducers and may be coupled to the controller 110 which may include transducer driving electronics to drive the transducers 142 as desired. The transducer array 146 is described in more detail in the Ser. No. 15/119,039 application.

In yet other embodiments, the catheter may include a suitable flexible member such as a guide wire which may be steerable and may be configured to guide the catheter, an optional instrument of the present system such as a UTA, a transducer array of a UTA, a scalpel, etc. to and/or from a desired location such as in the LIMA.

A process of performing a bypass procedure to bypass a desired portion of a target artery using a graft artery will now be described. For the sake of clarity, it will be assumed that the graft artery is a LIMA and the target artery is a LAD. Accordingly, a LIMA-LAD bypass process performed by the flexible apparatus in accordance with embodiments of the present system will now be described for the sake of clarity. However, it is also envisioned that embodiments of the present system may be applied to perform a different bypass procedure using the same or other suitable arteries, etc. if desired. Further, in some embodiments, the catheter may be coupled to an external base and/or control portion. However, in yet other embodiments, it is envisioned that the catheter may include a free body having at least one free end such as steerable snake-like robot (e.g., having at least one of first and second ends which are free) that are not coupled mechanically to any external base for support during at least part of a surgical process. Further, the catheter may communicate with a controller using any suitable method such as wired and wireless transmission methods. Moreover, in some embodiments, it is envisioned that a wireless power transmission circuit may be provided for wirelessly transmitting power to the catheter. In some embodiments, it is envisioned that the catheter may be configured by hardware, software (e.g., suitable programming of the controller), or a combination thereof to autonomously perform a coronary bypass procedure.

Figure 7:
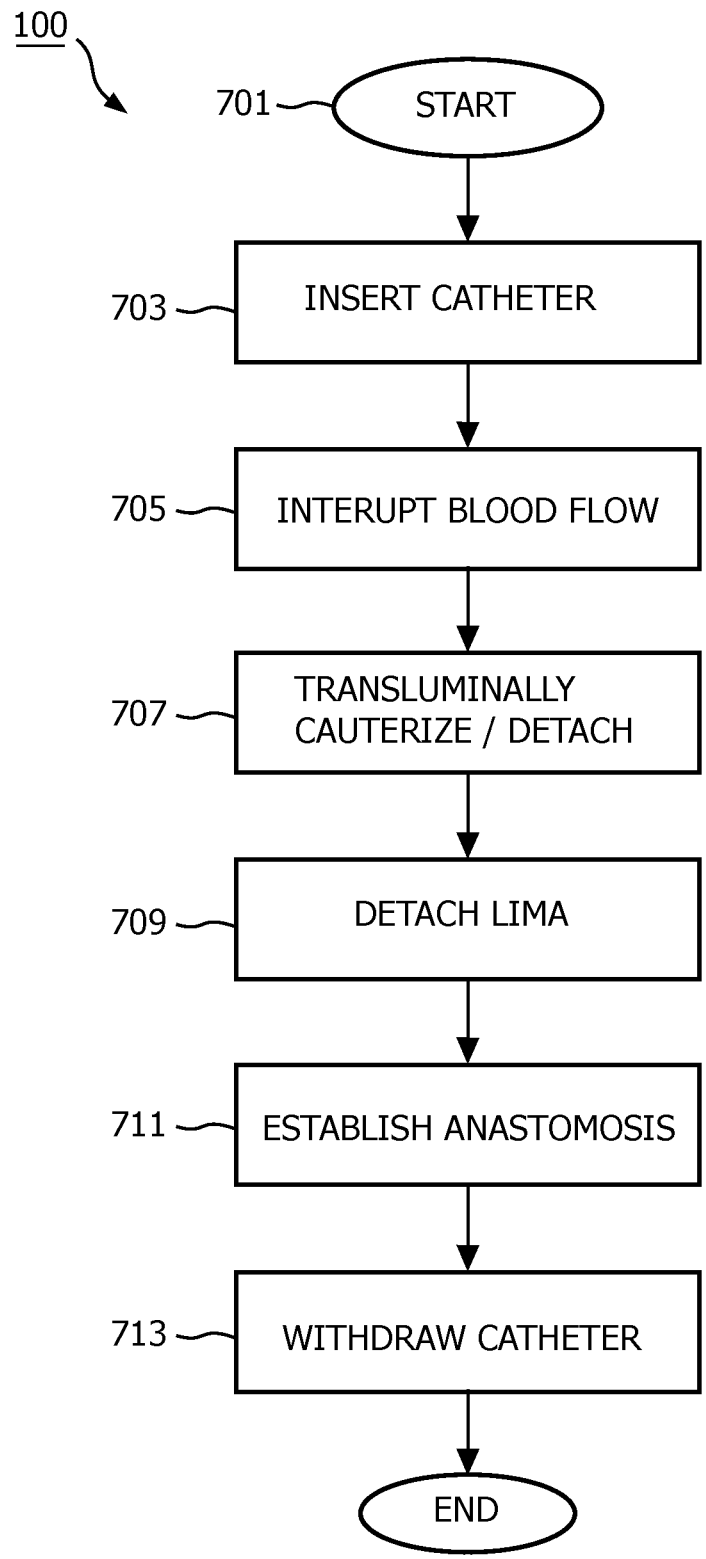
FIG. 7 is a flow diagram that illustrates a process performed by a system in accordance with embodiments of the present system.

FIG. 7 is a flow diagram that illustrates a process 700 performed by a system in accordance with embodiments of the present system. The process may perform a transluminal revascularization process such as a transluminal bypass process. The process 700 may be performed using one or more computers communicating over a network and may obtain information from, and/or store information to one or more memories which may be local and/or remote from each other. In accordance with embodiments of the present system, one or more of the acts may be performed using manual input from an operator who for example may take cues from pre- and/or intra-operative imaging. The process 700 can be performed using, inter alia, a flexible device such as a catheter 100 operating in accordance with embodiments of the present system and may include one of more of the following acts. Further, one or more of these acts may be combined and/or separated into sub-acts, if desired. Further, one or more of these acts may be skipped depending upon settings. In operation, the process may start during act 701 and then proceed to act 703. The acts of process 703 may be illustrated with reference to FIGS. 8A through 8D each of which shows a catheter such as the catheter 100 operating in accordance with embodiments of the present system.

Acts of the process may be illustrated with reference to FIGS. 8A through 9B. For example, FIGS. 8A, 8B, 8C and 8D show the catheter 100 during use performing acts of the process 700 in accordance with embodiments of the present system.

Referring back the process 700, during act 703, a catheter (such as the catheter 100) operating in accordance with embodiments of the present system may be inserted into a suitable location such as a LIMA of a mammal (hereinafter patient for the sake of clarity). This may be performed using any suitable method such as by insertion of the catheter through a femoral artery, over the aortic arch, into the left subclavian artery, and into the LIMA as shown in FIG. 8A. The catheter may be actively or passively steered to its desired location. For example, in some embodiments, a navigation-assisted imaging method such as a navigation-assisted X-ray method may be used to determine a location and/or orientation of one or more portions of the catheter relative to the patient and the controller may control the catheter to actively steer the catheter to the desired location and/or to a desired orientation. However, in yet other embodiments, a guide wire may be inserted into the LIMA and the catheter may be inserted over the guide wire so that the catheter may be guided into position by the guide wire. However, in accordance with embodiments of the present system, the catheter may be manually and/or robotically inserted. Arrow 807 shows an insertion direction for inserting the catheter. The process may insert and/or withdraw (e.g., in the direction opposite to arrow 807) the catheter 100 as desired. After completing act 703, the process may continue to act 705.

During act 705, the process may interrupt blood flow through the LIMA. The process may do this using any suitable method such as by inflating a balloon (e.g., 113) on the catheter, on a guide wire or otherwise. Accordingly, for example, the controller may actuate a pump, which is flow coupled to the balloon, to pump a fluid such as a gas (e.g., air, a noble gas (e.g., nitrogen, helium, etc.) or other fluid into the balloon so as to cause the balloon to expand. The controller may use any suitable imaging technique to confirm whether there is blood flowing in the LIMA, and if it is determined that blood is flowing in the LIMA, the controller may control the pump to continue pumping the fluid into the balloon. However, if it is determined that blood is not flowing in the LIMA, the controller may control the pump to cease pumping the fluid and to hold the fluid pressure by activating a flow-control valve to maintain pressure in the cavity of the balloon. However, in yet other embodiments, the flow-control valve may passively stop fluid flow from the cavity of the balloon until activated, at which time, the flow control valve may release pressure in the cavity of the balloon. In some embodiments, rather than using a pump, a pressurized fluid (e.g., gas) supply may be provided through, for example, a gas supply line. Accordingly, in these embodiments, a fluid control valve in flow communication with the pressurized fluid supply may be controlled by, for example, the controller, to provide fluid to, or remove fluid from, the balloon. In yet other embodiments, a mechanically controlled pump and/or flow-control valve may be provided and may be operated by the user. After completing act 705, the process may continue to act 707.

During act 707, the process may transluminally cauterize side branches of the LIMA and may detach LIMA from surrounding connective tissue using ultrasound signals. For example, the controller may drive a UTA to transmit focused ultrasound pulses (e.g., histotripsy pulses) to fractionate the connective tissue. The controller may control position and/or orientation of the UTA so that selected connective tissue such as connective tissue between lines 803 and 805 may be fractionated and the LIMA may be removed from the fractionated connective tissue. The controller may be operative to rotate the UTA about its longitudinal axis and/or move the UTA along a path of the LIMA so that all selected connective tissue may be fractionated. For example, the controller may distinguish tissue which has been fractionated from tissue that has not (e.g., of the connective tissue) and be operated to control the UTA to only fractionate the tissue which is determined not to have been fractionated. Accordingly, the controller may map tissue that has been fractionated so that it may be distinguished from tissue that has not been fractionated or may map location and/or orientation of the UTA. Further, in some embodiments, the controller may determine which transducers of the UTA to drive so that only the tissue that has not been fractionated may be subject to the histotripsy pulses emitted by the UTA.

The side branches of the LIMA may be transluminally cauterized using any suitable method such as by using by high-intensity focused ultrasound (HIFU) pulses that are lower in intensity but longer duration (e.g., when compared to the histotripsy pulses). These HIFU pulses may be emitted by the UTA using the same or separate transducers which provide the histotripsy pulses and may thermally coagulate tissue and blood to stop or otherwise restrict blood flow. However, in yet other embodiments, a trans-catheter cauterizer may be controlled by the controller to transluminally cauterize the side branches of the LIMA. Further, methods to detach the LIMA from the surrounding tissue and/or cauterize the side branches of the LIMA are discussed in the Ser. No. 15/119,039 application.

With regard to determining locations at which the LIMA is to be removed from connective tissue, cauterized, and cut, these locations may be determined by the user and/or process. For example, in some embodiments, the controller may analyze information obtained from a navigation-assisted imaging methods and may determine portions of the LIMA which should be separated from the connective tissue based upon analysis of the image information. For example, based upon an analysis of the anatomy of the patient, the controller may determine a path along the LIMA that should be separated from the connective tissue.

For example, with reference to FIG. 8A and in accordance with embodiments of the present system, the process may obtain image information of region-of-interest (ROI) which may include a heart 801 and LIMA of a patient and render a corresponding image (e.g., a 2D or 3D image) in real-time for the convenience of the user as shown in image 800A of FIG. 8A. Then, using the image information, the process may determine, using any suitable image processing method, a connection point (CP) on the LAD at which point the LIMA is to be coupled to, automatically or based upon a user selection and/or in accordance with physiology of the patient. Then, once the CP is established, the process may determine a path of the LIMA and may further determine a starting area (SA) as set forth by line 803 and length of the LIMA necessary to reach the connection point (CP). The process may then determine an ending area (EA) as set forth by line 805 at which the LIMA is to be cut (e.g., to form a distal end of the LIMA) in accordance with the starting area (SA) and the length of the LIMA necessary to reach the connection point (CP). This length may be known as a disconnection length ($LIMA_{DL}$) and may define an area in which the LIMA is disconnected from connective tissue. The ending area (EA) may be determined to be located along a path of the LIMA that begins at the starting area (SA) and extends for the length of the $LIMA_{DL}$. In other words, knowing the starting area (SA), the ending area (EA) may be located by adding the $LIMA_{DL}$ to SA. However, in yet other embodiments, it is envisioned that the ending area (EA) and the CP may be determined first and then the process may determine the $LIMA_{DL}$ accordingly.

In some embodiments, the process may provide a user interface such as a graphical user interface (GUI) with which the user (e.g., a surgeon) may (graphically or otherwise) select one of more of the CP, EA, SA, and $LIMA_{DL}$, using any suitable pointing device. Then, based upon the determined anatomy of the patient, the process may solve for the variables that were not selected by the user in accordance with information of the selected variables. For example, if a user selects the locations for the CP and SA, the process may determine the length of the $LIMA_{DL}$ and the EA accordingly, and may highlight a proposed $LIMA_{DL}$ and EA for the convenience of the user. Accordingly, a user may approve of the proposed locations or may make changes, if desired and the process may respond accordingly. Further, the process may predict what at least portions of the LIMA and heart 801 would look like assuming a bypass was performed using proposed settings for one or more of the SA, EA, CP, and $LIMA_{DL}$ and render a corresponding image so that the user may determine whether any changes are desired to one or more of the SA, EA, CP, and $LIMA_{DL}$ and may enter these changes so that the process may update one or more of the SA, EA, CP, and $LIMA_{DL}$ accordingly.

For example, illustratively with reference to FIG. 8A, the path along the LIMA that should be separated from the connective tissue is situated between dotted lines 803 and 805 and the LIMA should be cut at line 805. Once determining the path along the LIMA that should be separated from the connective tissue, the process may superimpose this information and/or an image depicting a position of the catheter 100 on an image of the heart 801 of the patient and render this information in real-time on a display of the system for the convenience of the user as shown in FIG. 8A. However, in yet other embodiments, it is envisioned that the user may manually control the catheter 100 to disconnect the LIMA from the connective tissue and/or cauterize the side branches of the LIMA, if desired. In some embodiments, the controller may control the position and/or orientation of the catheter within the LIMA as may be necessary.

For example, illustratively the LIMA may be cut at line 805 using any suitable method such as transluminally using any suitable scalpel such as an ultrasonic scalpel, a laser scalpel etc. or using any suitable external scalpel. The cutting may be performed automatically by the controller, if desired or a combination of manual and automatic control of the suitable cutting method may be performed in accordance with embodiments of the present system. After completing act 707, the process may continue to act 709.

Figure 8D:
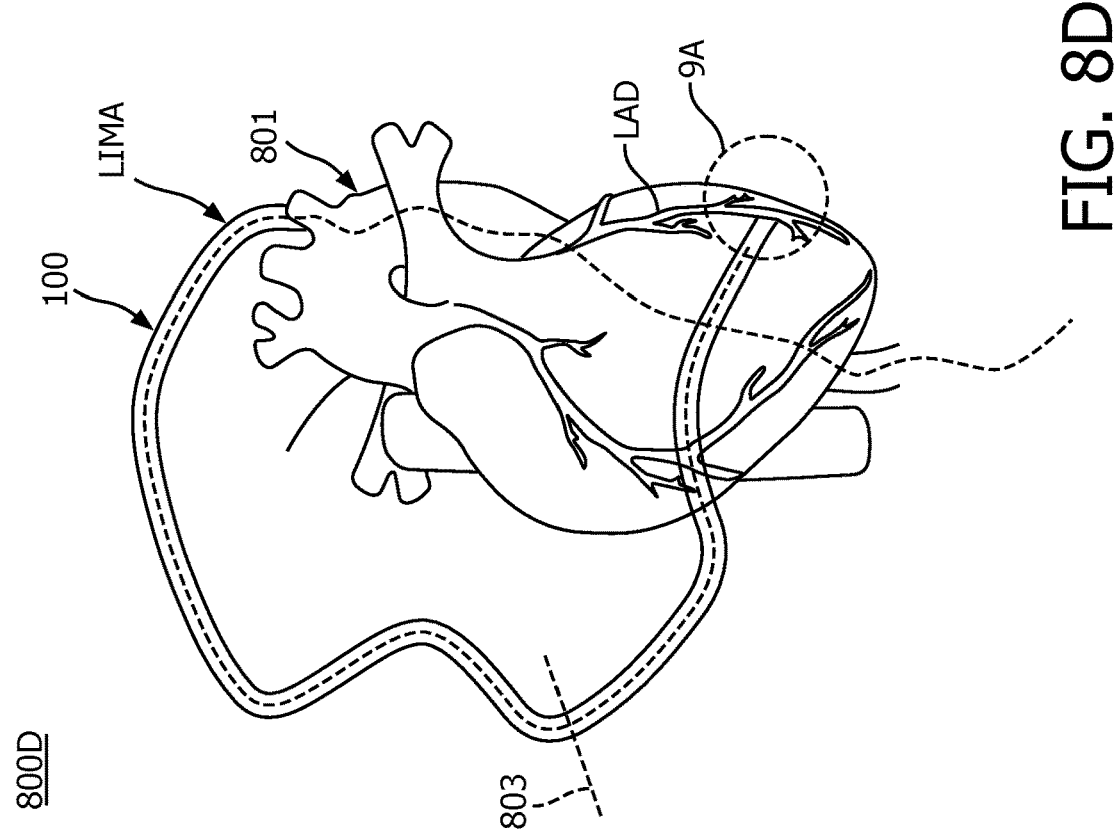
FIG. 8D shows the catheter 100 during use performing acts of process 700 in accordance with embodiments of the present system.
Figure 8C:
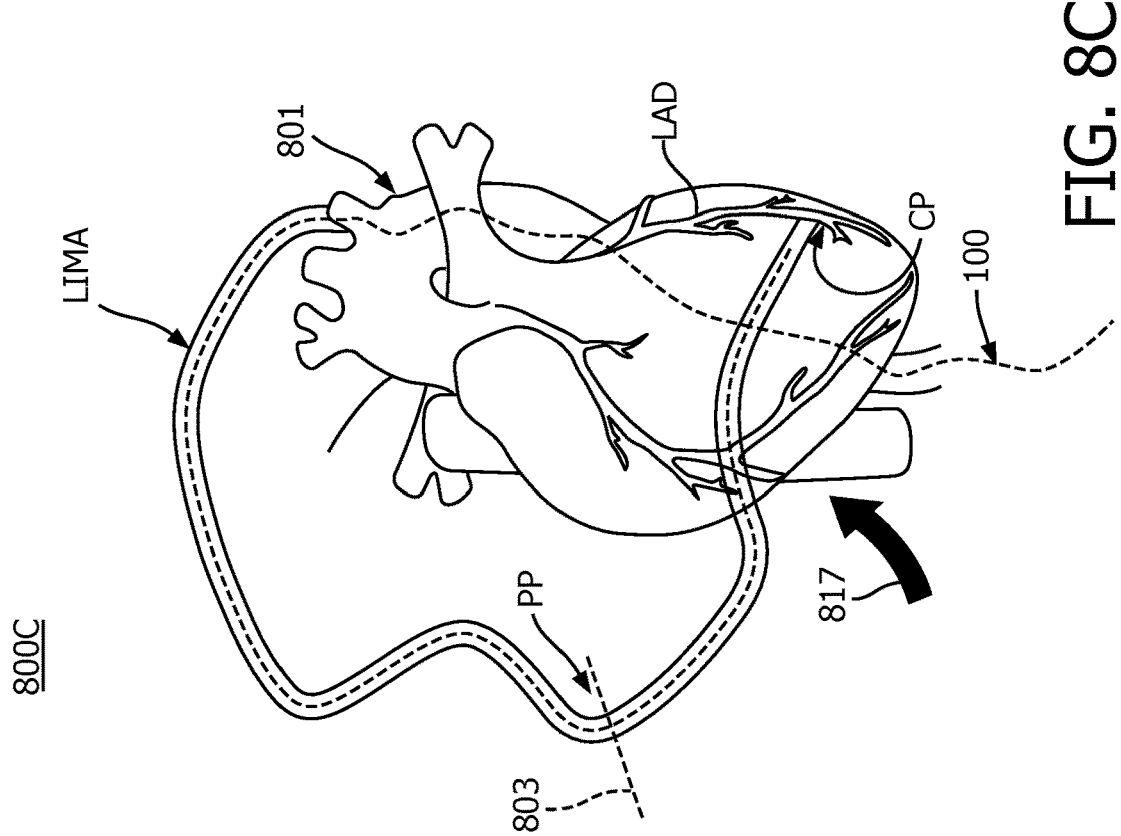
FIG. 8C shows the catheter 100 during use performing acts of process 700 in accordance with embodiments of the present system.

During act 709, the process may control the catheter to apply a force to remove (e.g., by mechanically detaching or uncoupling) at least the detached portion of the LIMA from the chest wall and to guide at least the distal end of the LIMA toward the desired bypass location (e.g., CP) as illustrated by arrows 817 of FIGS. 8B and 8C. Depending on the location of the anastomosis as well as on the length of LIMA, a part of the LIMA may optionally remain attached to connective tissue and, thus, the chest wall, if desired. Accordingly, the portion of the LIMA that optionally remains attached to the connective tissue may be used as an anchor or a pivot point (PP) and may be generally located at the SA. However, in an embodiment wherein the entire LIMA is detached from the connective tissue of the chest wall, a portion of the catheter may be controlled to remain fixed (e.g., by remaining rigid or substantially rigid) in order to provide an anchor to a portion of the catheter (e.g., to stabilize at least a portion of the catheter) when controllably steering the catheter to guide the LIMA (e.g., automatically and/or by manual input of a user) to the desired bypass location (e.g., CP). During this process, guidance of the flexible device to the desired bypass location can be performed using any suitable real-time navigation-assisted imaging method such as an intraoperative X-ray as may be performed in a percutaneous coronary intervention or the like. After it is determined that the distal end of the LIMA is placed (e.g., by the catheter situated within) at the bypass location (e.g., as shown in FIG. 8D), the process will continue to act 711.

During act 711, the process may establish an anastomosis (e.g., a coupling) between the LIMA (e.g., graft vessel) and the LAD (e.g., the target vessel) at the CP using any suitable method. The LIMA to LAD coupling may establish (blood) flow communication (e.g., bypass) from the LIMA to the LAD as shown in FIG. 8D. To form the (flow) coupling, for example, in accordance with some embodiments, an arterial puncture device may be passed through a channel of the catheter and through an adjacent wall of the LAD to establish a port in the LAD for revascularization under the control of the controller.

However, in yet other embodiments, a laser arteriectomy device, such as an excimer laser-assisted nonocclusive anastomosis (ELANA) laser, an anastomosis catheter or the like may be used to provide a suitable cutting such as a precise circular cut in the LAD so as to establish a port in the LAD. In yet other embodiments, the catheter may include a laser arteriectomy device situated at the distal end of the catheter to establish the port in the LAD.

Regardless of the method used to establish the port in the LAD, after the port is established, the process may optionally place a stent graft such as an endoluminal stent graft (such as a JOSTENT™ GRAFTMASTER™ stent graft used for punctured coronary arteries by Abbot Vascular) or the like at the interface between the LIMA and the LAD using the catheter. The stent graft may be passed through a channel of the catheter using any suitable method and may be placed at the target location as desired. The stent graft may expand against the walls of the LAD and LIMA to ensure good purchase within each vessel. In addition, it may be fenestrated or a continuous tube as required. In some embodiments multiple interlocking (i.e. a fenestrated stent graft in the LAD with a standard stent interlocking through the fenestration) and/or branched stent grafts and/or pre-shaped stent grafts may be used. It is further envisioned that the stent graft may include hooks (such as provided by the Anaconda™ stent system by Vascutek) to facilitate attachment and/or another attachment system may be provided as desired such as suturing.

Figure 9A:
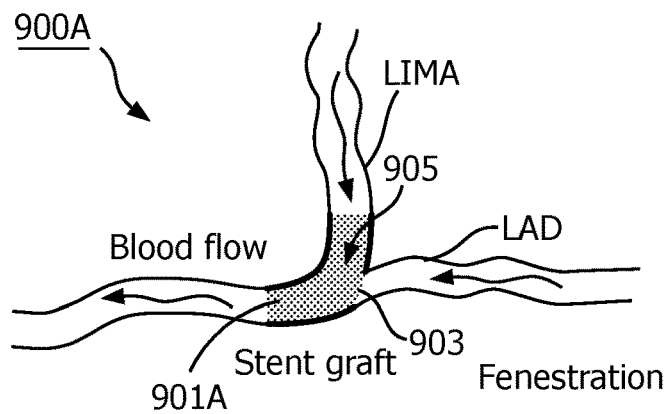
FIG. 9A shows a detailed view of a portion of the coupling area 9A shown in FIG. 8D in accordance with embodiments of the present system.
Figure 9B:
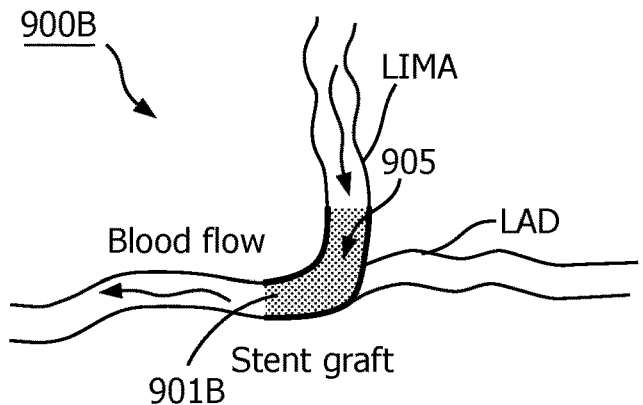
FIG. 9B shows a detailed view of a coupling area that is similar to the coupling area shown in FIG. 9A in accordance with embodiments of the present system.
Figure 9C:
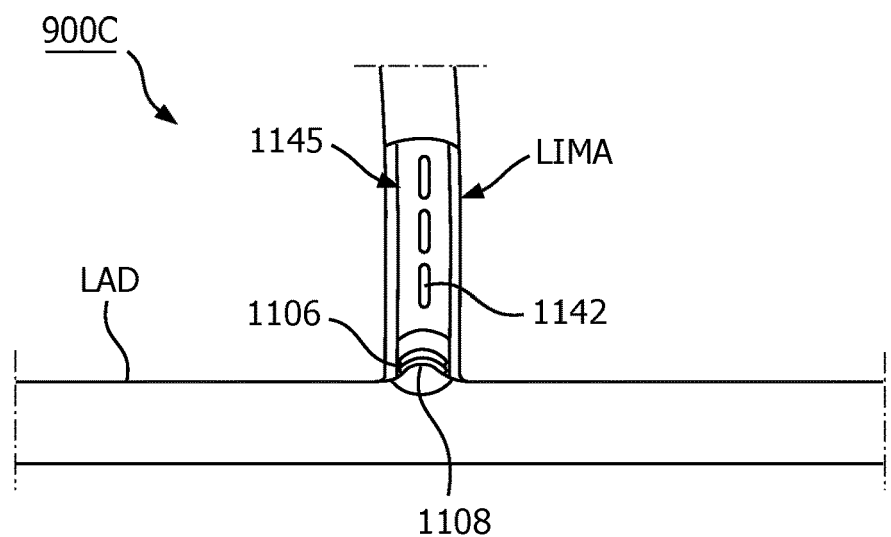
FIG. 9C shows a detailed view of a process of cutting the LAD using an integrated UTA in accordance with embodiments of the present system.
Figure 10:
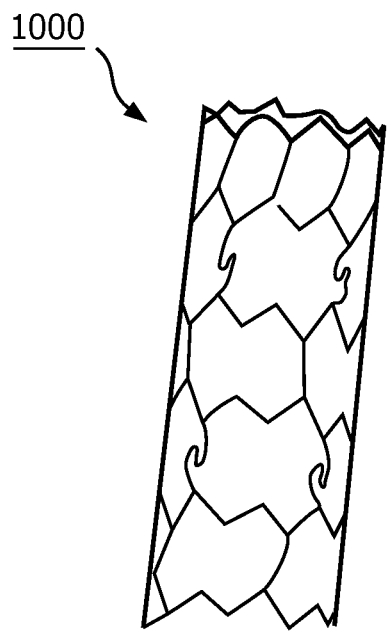
FIG. 10 shows a side view of the JOSTENT™ GRAFT-MASTER™ stent graft.

FIG. 9A shows a detailed view of a portion of the coupling area 9A shown in FIG. 8D in accordance with embodiments of the present system. The coupling area includes a fenestrated stent graft 901A which is inserted into a port 905 situated in the LAD and configured such that blood flow downstream of the fenestrated stent graft 901A (such as the JOSTENT™ GRAFTMASTER™ stent graft) may be received from one or more of the LIMA and LAD. FIG. 10 shows a side view of the JOSTENT™ GRAFTMASTER™ stent graft. FIG. 9B shows a detailed view of a coupling area that is similar to the coupling area shown in FIG. 9A in accordance with embodiments of the present system. FIG. 9B is similar to FIG. 9A, however, a stent graft 901B which is not fenestrated is provided rather than the fenestrated stent graft 901A of FIG. 9A. Accordingly, in the embodiment shown in FIG. 9B, blood flow along the LAD is totally occluded. FIG. 9C shows a detailed view of a process of cutting the LAD using an integrated UTA in accordance with embodiments of the present system.

Figure 11A:
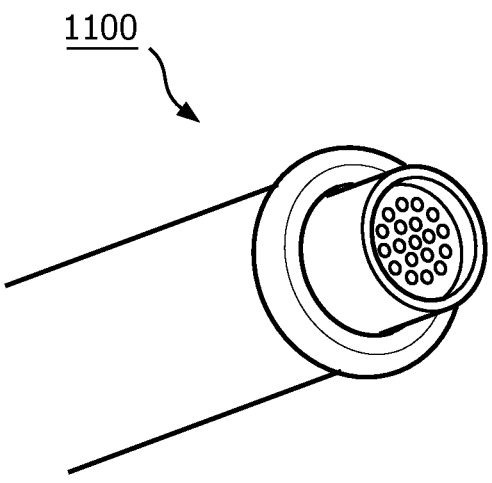
FIG. 11A shows a front perspective view of a portion of an ELENA™ laser anastomosis catheter.

FIG. 11A shows a front perspective view of a portion of an ELENA™ laser anastomosis catheter 1100A that may be suitably utilized in accordance with embodiments of the present system.

Figure 11B:
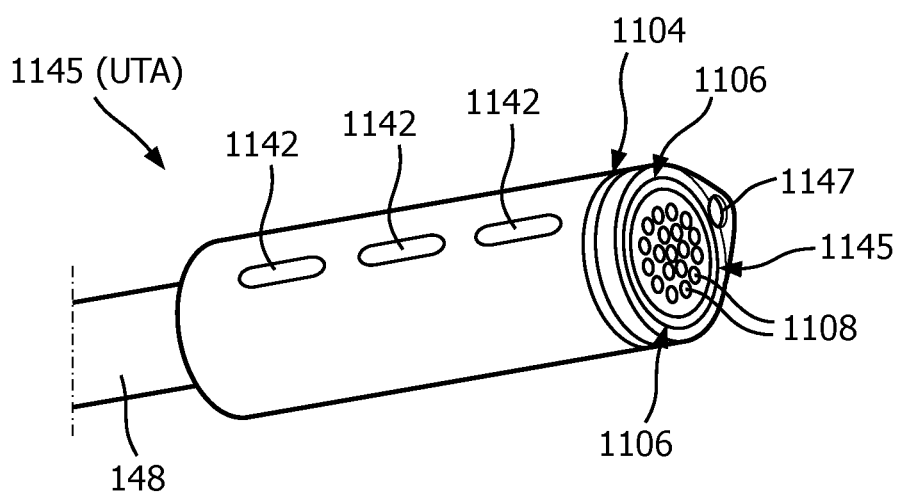
FIG. 11B shows a front perspective view of portion of an integrated UTA in accordance with embodiments of the present system.

FIG. 11B shows a front perspective view of portion of an integrated UTA 1145 in accordance with embodiments of the present system. The UTA 1145 may be similar to the UTA 145 and may include at least one ultrasonic transducer 1142 which is similar to the ultrasonic transducers 142. However, the UTA 1145 may include first and second laser anastomosis catheters 1104 and 1106, respectfully, and at least one suction port 1108. The second laser anastomosis catheters 1106 may be controlled (e.g., by the controller) to cut the LIMA at the EA so as to form a distal end of the LIMA which may be coupled to the LAD. Referring FIGS. 9C and 11B, and in accordance with embodiments or the present system, the first laser anastomosis catheter 1104 may be controlled (e.g., by the controller) to cut a (disc-like) portion of the LAD so as to establish a port to be flow coupled to the LIMA and which may be configured to receive, for example, a stent graft. During the cutting process, a vacuum may be applied through the at least one suction port 1108 to hold the portion of the LAD that is to be cut away. Thereafter, the portion of the LAD that is cut away may be pulled away from the port, and a stent graft may be placed through the port and into at least a portion of the LAD using a stent applicator instrument which may extend from an opening 1147 which lies to a side of the first laser anastomosis catheter 1104 and, thus, is not covered by the portion of the LAD that is cut away.

Referring back to FIG. 7, after anastomosis (e.g., a coupling) between the LIMA and the LAD is established, the revascularization may be complete and the process may continue to act 713.

During act 713, the process may withdraw the catheter from the LIMA. Accordingly, in accordance with some embodiments, the controller may control actuators to withdraw the catheter from at least the LIMA. Then, the process may continue to act 715, where it may end.

Figure 12:
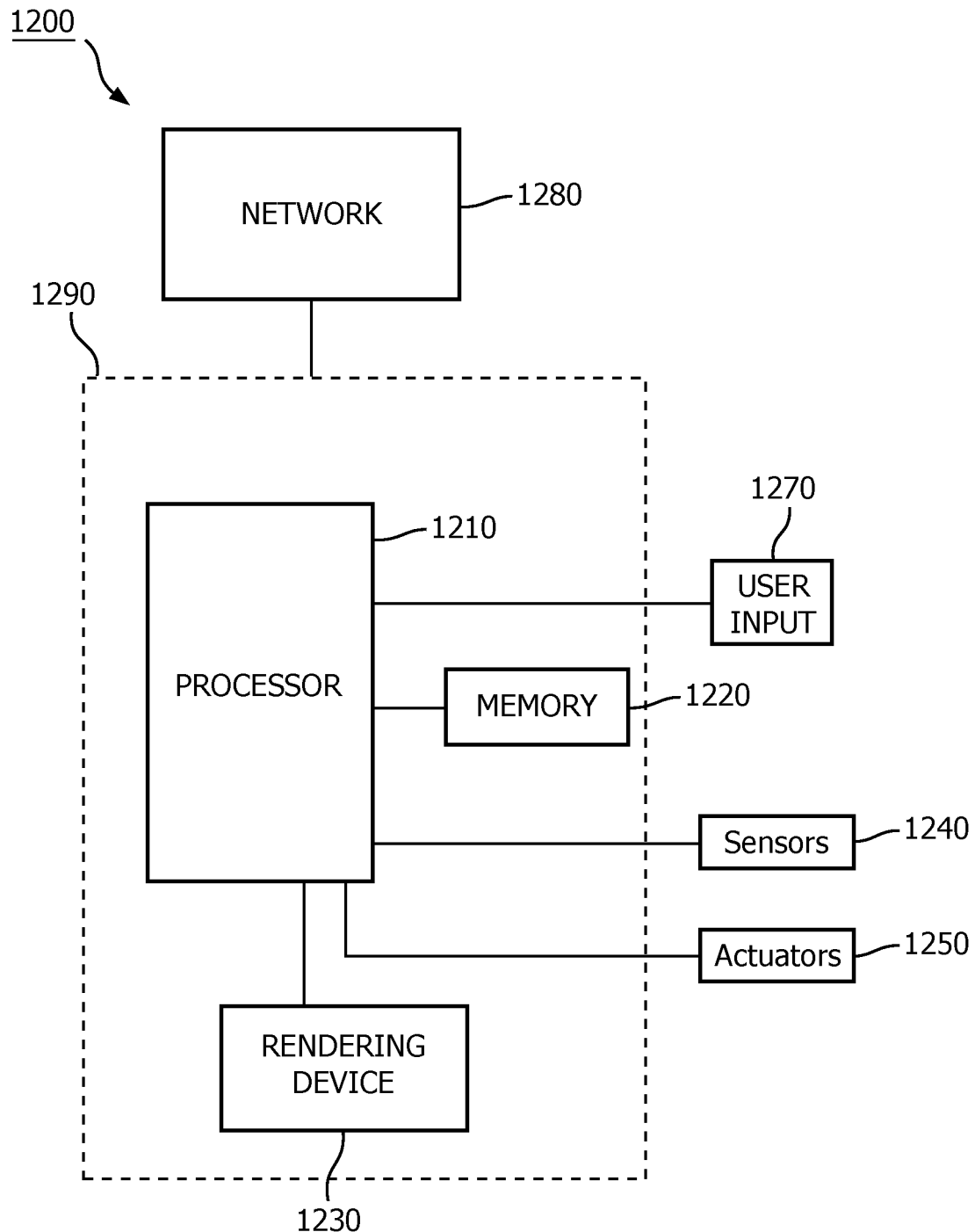
FIG. 12 shows a portion of a system in accordance with embodiments of the present system.

FIG. 12 shows a portion of a system 1200 in accordance with embodiments of the present system. For example, a portion of the present system 1200 may include a processor 1210 (e.g., a controller) operationally coupled to a memory 1220, a user interface 1230 (e.g., a display), sensors 1240, actuators 1250, and a user input device 1270. The memory 1220 may be any type of device for storing application data as well as other data related to the described operation. The application data and other data are received by the processor 1210 for configuring (e.g., programming) the processor 1210 to perform operation acts in accordance with the present system. The processor 1210 so configured becomes a special purpose machine particularly suited for performing in accordance with embodiments of the present system. The sensors may include sensors of a catheter in accordance with embodiments of the present system. For example, the sensors may include imaging sensors, position sensors (e.g., linear, rotational, deflection, etc.), temperature sensors, pressure sensors, flow sensors, status sensors, etc. each of which may provide corresponding information to the controller 1210 for further processing.

The operation acts may include configuring the system 1200 by, for example, configuring the processor 1210 to obtain information from user inputs, the sensors 1240, and/or the memory 1220 and processing this information in accordance with embodiments of the present system to obtain information related to use of the catheter in accordance with embodiments of the present system. The user input portion 1270 may include a keyboard, a mouse, a trackball, rotational wheels, a joystick, and/or other device, including touch-sensitive displays, which may be stand alone or be a part of a system, such as part of a personal computer, a notebook computer, a netbook, a tablet, a smart phone, a personal digital assistant (PDA), a mobile phone, and/or other device for communicating with the processor 1210 via any operable link. The user input portion 1270 may be operable for interacting with the processor 1210 including enabling interaction within a UI as described herein. Clearly the processor 1210, the memory 1220, the UI 1230, the actuators 1250, and/or user input device 1270 may all or partly be a portion of a computer system or other device such as a client and/or server as described herein.

Operation acts may include requesting, providing, and/or rendering of information such as, for example, information related navigation-assisted imaging methods to determine location of one or more portions of the catheter within a patient during surgery. The processor 1210 may render the information on the UI 1230 such as on a display of the system such as status information, image information (e.g., in real-time) which may include images in a region-ofinterest. The sensors may include suitable sensors to provide desired sensor information to the processor 1210 for further processing in accordance with embodiments of the present system.

The methods of the present system are particularly suited to be carried out by processor programmed by a computer software program, such program containing modules corresponding to one or more of the individual steps or acts described and/or envisioned by the present system.

The processor 1210 is operable for providing control signals and/or performing operations in response to input signals from the user input device 1270 as well as in response to other devices of a network and executing instructions stored in the memory 1220. For example, the processors 1210 may obtain feedback information from the sensors 1240 and may process this information to position, orientation, and/or status of portions of the catheter. The processor 1210 may determine actions to perform in accordance with embodiments of the present system. The processor 1210 may control the actuators to perform corresponding actions. The actuators may include motors (e.g., linear, rotational, etc.), pumps, electro-active polymers (EAPs), scalpels (e.g., laser, etc.), ultrasound transducers, lasers, amplifiers, switches, etc. The processor 1210 may include one or more of a microprocessor, an application-specific or general-use integrated circuit(s), a logic device, etc. Further, the processor 1210 may be a dedicated processor for performing in accordance with the present system or may be a general-purpose processor wherein only one of many functions operates for performing in accordance with the present system. The processor 1210 may operate utilizing a program portion, multiple program segments, and/or may include or be a hardware device utilizing a dedicated or multi-purpose integrated circuit.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention.

Accordingly, embodiments of the present system provide for a flexible device (such as a catheter) and method to perform acts such as: percutaneously accessing a LIMA; transluminally forming and removing a distal portion of the LIMA from the chest wall, steering the flexible device and the LIMA in which the flexible device is located towards a selected bypass site on a diseased artery (such as a coronary artery) and/or attaching the LIMA to the bypass site so as to establish flow communication between the LIMA and the diseased artery. Accordingly, an optimal coronary revascularization combining effectiveness of LIMA-LAD bypass with the minimally invasive approach of stenting may be provided in accordance with embodiments of the present system.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

The invention claimed is:

1. A method of performing a bypass procedure, the method performed by a flexible apparatus controlled by at least one controller, the method comprising acts of:

percutaneously situating the flexible apparatus through a first artery which is coupled to connective tissue of a chest wall;

transluminally detaching at least a portion of the first artery surrounding the flexible apparatus to thereby detach the first artery from the connective tissue of the chest wall by applying ultrasound signals of a first type emitted by a plurality of elongated spherical transducers arranged longitudinally in a row rotationally coupled to a distal end of the flexible apparatus while rotating the plurality of elongated spherical transducers about a longitudinal axis of the flexible apparatus;

driving at least one of the plurality of elongated spherical transducers to emit ultrasound signals of the first type to transluminally fractionate the portion of the first artery surrounding the flexible apparatus to thereby detach the portion of the first artery surrounding the flexible apparatus from a distal portion of the first artery;

steering at least the detached portion of the first artery surrounding the flexible apparatus from a current location to a bypass location at a target artery by applying a force transmitted through the flexible apparatus situated within the first artery;

establishing a port in the target artery at the bypass location with an arteriectomy device attached around a distal tip of the flexible apparatus; and coupling, by the flexible apparatus situated within the first artery, the first artery to the target artery at the bypass location to establish flow communication between the first artery and the target artery.

2. The method of claim 1, further comprising an act of at least partially interrupting blood flow through the first artery by inflating a balloon situated about an outer periphery of the flexible apparatus.

3. The method of claim 1, further comprising acts of inserting a stent graft through a channel in the flexible apparatus and at least partially through the port in the target artery; and attaching the stent graft to the target artery.

4. The method of claim 1, further comprising an act of transluminally cauterizing side branches of the first artery by applying ultrasound signals of a second type emitted by at least one of the plurality of elongated spherical transducers of the flexible apparatus.

5. The method of claim 4, wherein the ultrasound signals of the first type comprise histotripsy pulses and the ultrasound signals of the second type comprise high-intensity focused ultrasound (HIFU) pulses that are lower in intensity and longer in duration than the ultrasound signals of the first type.

6. The method of claim 1, wherein the first artery is a left internal mammary artery (LIMA) and the target artery is a left anterior descending artery (LAD).

7. A flexible apparatus for performing a bypass procedure, the flexible apparatus comprising:

a flexible body;

a plurality of elongated spherical transducers arranged longitudinally in a row rotationally coupled to a distal end of the flexible body;

at least one laser arteriectomy device attached around a distal tip of the flexible body;

at least one controller which is configured to:

percutaneously locate the flexible apparatus into at least one desired location of a first artery which is coupled to connective tissue of a chest wall;

drive the plurality of elongated spherical transducers to emit ultrasound signals of a first type while rotating the plurality of elongated spherical transducers about a longitudinal axis of the flexible body to transluminally detach at least a portion of the first artery surrounding the flexible body from the connective tissue;

drive at least one of the plurality of elongated spherical transducers (142) to emit ultrasound signals of the first type to transluminally fractionate the portion of the first artery surrounding the flexible body to thereby detach the portion of the first artery surrounding the flexible body from a distal portion of the first artery;

steer the flexible body to move the detached portion of the first artery surrounding the flexible body from a current location to a bypass location at a target artery;

establish a port in the target artery at the bypass location with the at least one laser arteriectomy device; and couple the first artery to the target artery at the bypass location to establish flow communication between the first artery and the target artery.

8. The flexible apparatus of claim 7, wherein the at least one controller is further configured to at least partially interrupt blood flow through the first artery by inflating a balloon situated about an outer periphery of the flexible body proximate to the plurality of elongated spherical transducers.

9. The flexible apparatus of claim 7, wherein the at least one controller is further configured to insert a stent graft through a channel in the flexible body and at least partially through the port in the target artery and attach the stent graft to the target artery.

10. The flexible apparatus of claim 7, wherein the at least one controller is further configured to transluminally cauterize side branches of the first artery by applying ultrasound signals of a second type emitted by at least one of the plurality of elongated spherical transducers.

11. The flexible apparatus of claim 10, wherein the at least one controller is further configured to drive the at least one transducer such that the ultrasound signals of the first type comprise histotripsy pulses and the ultrasound signals of the second type comprise high-intensity focused ultrasound (HIFU) pulses that are lower in intensity and longer in duration than the ultrasound signals of the first type.

12. A computer program stored on a non-transitory computer readable memory medium, the computer program configured to control a flexible apparatus to perform a bypass procedure, the computer program comprising:

a program portion configured to control the flexible apparatus to:

percutaneously locate the flexible apparatus into a first artery which is coupled to connective tissue of a chest wall;

transluminally fractionate at least a portion of the first artery surrounding the flexible apparatus to thereby detach the first artery from the connective tissue of the chest wall by applying ultrasound signals of a first type emitted by a plurality of elongated spherical transducers arranged longitudinally in a row rotationally coupled to a distal end of the flexible apparatus while rotating the plurality of elongated spherical transducers about a longitudinal axis of the flexible apparatus;

drive at least one of the plurality of elongated spherical transducers to emit ultrasound signals of the first type to transluminally fractionate the portion of the first artery surrounding the flexible apparatus to thereby detach the portion of the first artery surrounding the flexible apparatus from a distal portion of the first artery;

steer the detached portion of the first artery surrounding the flexible apparatus from a current location to a bypass location at a target artery by applying a force transmitted through the flexible apparatus situated within the first artery;

establish a port in the target artery at the bypass location with an arteriectomy device attached around a distal tip of the flexible apparatus; and couple, by the flexible apparatus situated within the first artery, the first artery to the target artery at the bypass location to establish flow communication between the first artery and the target artery.

13. The computer program of claim 12, wherein the program portion is further configured to at least partially interrupt blood flow through the first artery by inflating a balloon situated about an outer periphery of the flexible apparatus.

14. The computer program of claim 12, wherein the program portion is further configured to insert a stent graft through a channel in the flexible apparatus and at least partially through the port in the target artery.

15. The computer program of claim 12, wherein the program portion is further configured to transluminally cauterize side branches of the first artery by applying ultrasound signals of a second type emitted by the plurality of elongated spherical transducers of the flexible apparatus.

16. The computer program of claim 15, wherein the ultrasound signals of the first type comprise histotripsy pulses and the ultrasound signals of the second type comprise high-intensity focused ultrasound (HIFU) pulses that are lower in intensity and longer in duration than the ultrasound signals of the first type.

* * * * *